US006475418B1

(12) United States Patent
Tsai et al.

(10) Patent No.: US 6,475,418 B1
(45) Date of Patent: *Nov. 5, 2002

(54) METHODS FOR MAKING A THERMOPLASTIC COMPOSITION AND FIBERS INCLUDING SAME

(75) Inventors: Fu-Jya Daniel Tsai, Appleton, WI (US); Brigitte C. Wertheim, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 189 days.

This patent is subject to a terminal disclaimer.

(21) Appl. No.: 09/606,571

(22) Filed: Jun. 29, 2000

Related U.S. Application Data

(62) Division of application No. 09/436,682, filed on Nov. 9, 1999, now Pat. No. 6,201,068, which is a continuation-in-part of application No. 09/222,094, filed on Dec. 29, 1998, now Pat. No. 6,211,294, which is a division of application No. 08/962,432, filed on Oct. 31, 1997, now Pat. No. 5,910,545.

(51) Int. Cl.$^7$ ................................................ D01D 5/26
(52) U.S. Cl. ................ 264/143; 264/176.1; 264/210.8; 264/211
(58) Field of Search ................................ 264/143, 148, 264/176.1, 210.8, 211

(56) References Cited

U.S. PATENT DOCUMENTS

| | | |
|---|---|---|
| 2,703,316 A | 3/1955 | Schneider |
| 3,531,561 A | 9/1970 | Trebu |
| 3,792,011 A | 2/1974 | Smith et al. |
| 3,853,820 A | 12/1974 | Vachon |
| 3,921,333 A | 11/1975 | Clendinning et al. |
| 3,964,486 A | 6/1976 | Blaney |
| 4,137,921 A | 2/1979 | Okuzumi et al. |
| 4,175,177 A | 11/1979 | Potts |
| 4,367,070 A | 1/1983 | Hayashi et al. |
| 4,489,056 A | 12/1984 | Himmelstein et al. |
| 4,685,909 A | 8/1987 | Berg et al. |
| 4,710,187 A | 12/1987 | Boland et al. |
| 4,762,521 A | 8/1988 | Roessler |
| 4,770,656 A | 9/1988 | Proxmire et al. |
| 4,789,592 A | 12/1988 | Taniguchi et al. |
| 4,798,603 A | 1/1989 | Meyer et al. |
| 4,800,219 A | 1/1989 | Murdoch et al. |
| 4,931,488 A | 6/1990 | Chiquet |
| 4,959,410 A | 9/1990 | Eichenauer et al. |
| 4,983,689 A | 1/1991 | Yu |
| 5,057,368 A | 10/1991 | Largman et al. |
| 5,069,970 A | 12/1991 | Largman et al. |
| 5,076,983 A | 12/1991 | Loomis et al. |
| 5,108,820 A | 4/1992 | Kaneko et al. |
| 5,147,712 A | 9/1992 | Miyahara et al. |
| 5,160,472 A | 11/1992 | Zachariades |
| 5,162,153 A | 11/1992 | Cooke et al. |
| 5,180,765 A | 1/1993 | Sinclair |
| 5,202,178 A | 4/1993 | Turner |
| 5,223,546 A | 6/1993 | Morita et al. |
| 5,238,968 A | 8/1993 | Morita et al. |
| 5,241,066 A | 8/1993 | Davis et al. |
| 5,252,642 A | 10/1993 | Sinclair et al. |
| 5,258,422 A | 11/1993 | Chang et al. |
| 5,273,596 A | 12/1993 | Newkirk |
| 5,277,976 A | 1/1994 | Hogle et al. |
| 5,286,770 A | 2/1994 | Bastioli et al. |
| 5,294,469 A | 3/1994 | Suzuki et al. |
| 5,321,068 A | 6/1994 | De Witt, Jr. |
| 5,336,552 A | 8/1994 | Strack et al. |
| 5,338,822 A | 8/1994 | Gruber et al. |
| 5,340,646 A | 8/1994 | Morita et al. |
| 5,382,400 A | 1/1995 | Pike et al. |
| 5,405,887 A | 4/1995 | Morita et al. |
| 5,412,005 A | 5/1995 | Bastioli et al. |
| 5,424,346 A | 6/1995 | Sinclair |
| 5,434,004 A | 7/1995 | Ajioka et al. |
| 5,444,113 A | 8/1995 | Sinclair et al. |
| 5,446,123 A | 8/1995 | Gruber et al. |
| 5,462,983 A | 10/1995 | Bloembergen et al. |
| 5,475,080 A | 12/1995 | Gruber et al. |
| 5,484,881 A | 1/1996 | Gruber et al. |
| 5,489,474 A | 2/1996 | Shinoda et al. |
| 5,500,465 A | 3/1996 | Krishnan et al. |
| 5,502,158 A | 3/1996 | Sinclair et al. |
| 5,508,378 A | 4/1996 | Ohara et al. |
| 5,525,706 A | 6/1996 | Gruber et al. |
| 5,545,681 A | 8/1996 | Honkonen |
| 5,593,778 A | 1/1997 | Kondo et al. |
| 5,637,631 A | 6/1997 | Kitada et al. |
| 5,691,424 A | 11/1997 | Suzuki et al. |
| 5,714,618 A | 2/1998 | Kimura et al. |
| 5,783,504 A | 7/1998 | Ehret et al. |
| 6,197,237 B1 * | 3/2001 | Tsai et al. .............. 264/172.13 |

FOREIGN PATENT DOCUMENTS

| | | |
|---|---|---|
| DE | 4016348 A | 11/1991 |
| EP | 0 312 118 A2 | 4/1989 |

(List continued on next page.)

OTHER PUBLICATIONS

Fedorova, R.G. et al. Chemical Abstracts 109(4)24162z, *Khim. Volokna* 2 11–12 1998 "Composite Fibers From Polyacrylonitrile–Aromatic Polyamic Acid Blends".

ASTM Designation: D 1238–95, "Standard Test Method for Flow Rates of Thermoplastics by Extrusion Plastomer," pp. 273–281 1996.

(List continued on next page.)

*Primary Examiner*—Leo B. Tentoni
(74) *Attorney, Agent, or Firm*—Kilpatrick Stockton LLP

(57) ABSTRACT

A disposable article including a biodegradable nonwoven material having improved fluid management properties. The nonwoven material may be produced using thermoplastic compositions which comprise an unreacted mixture of a poly(lactic acid) polymer; a polybutylene succinate polymer or a polybutylene succinate adipate polymer, or a mixture of such polymers; and a wetting agent. The thermoplastic composition exhibits substantial biodegradable properties yet is easily processed. The biodegradable nonwoven materials may be used in a disposable absorbent product intended for the absorption of fluids such as body fluids.

16 Claims, No Drawings

FOREIGN PATENT DOCUMENTS

| EP | 0394954 | | 10/1990 |
|---|---|---|---|
| EP | 0515203 | A2 | 11/1992 |
| EP | 0569153 | A2 | 11/1993 |
| EP | 0765913 | A1 | 4/1997 |
| JP | 5-71005 | | 3/1993 |
| JP | 5-140361 | A | 6/1993 |
| JP | 6-207320 | A | 7/1994 |
| JP | 6-207323 | A | 7/1994 |
| JP | 6-207324 | A | 7/1994 |
| JP | 6-248552 | A | 9/1994 |
| JP | 7-133511 | A | 5/1995 |
| JP | 8-134723 | A | 5/1996 |
| JP | 8-260320 | A | 10/1996 |
| WO | 92/04410 | A1 | 3/1992 |
| WO | 94/07941 | A1 | 4/1994 |
| WO | 94/08078 | A1 | 4/1994 |
| WO | 95/08660 | A1 | 3/1995 |
| WO | 95/17216 | A1 | 6/1995 |
| WO | WO 99/23163 | A1 | 5/1999 |

OTHER PUBLICATIONS

American Society for Testing Materials (ASTM) Designation: D 5338–92, Standard Test Method for Determining Aerobic Biodegradation of Plastic Materials Under Controlled Composting pp. 456–461 1993.

Slizite, G. et al. Chemical Abstracts 105(26)228372v, "Study of Photochemical Degradation of Articles Produced from Complex Triacetate–Polyamide Fiber" *Nauch. Tr. Vuzov LitSSR. Khimiya i Khim. Teknol.* 27 98–102 1986.

U, Ju Jui et al. Chemical Abstracts 106(12)86124k, "Use of a Reactively Dyed Low–Molecular–Weight Polycaproamide for Production of Colored Polypropylene Fibers" *Khim. Volokna* 6 22–24 1986.

Zhao Delu, Xue Du et al. Chemical Abstracts 105(12)99049u, "Applications of Controlled Degradation in Polypropylene Tape Yarns" *Suliao* 15 5–10 1986.

Zakirov, I.Z. Chemical Abstracts 102(22)186548n, "Temperature Transitions in Polyacrylonitrile–Fibroin Mixtures" *Vysokomol. Soedin., Ser. B* 27 116–120 1985.

Sagatova, M. Sh. et al. Chemical Abstracts 102(10)80131f, "Structural and Mechanical Properties of Fibers Produced From Mixtures of Polyacrylonitrile and Chlorinated Poly(vinyl chloride)" Viniti Deposited 939–8 Document 4 (10 pp.) 1984.

Dreizenshtok, G.S. et al. Chemical Abstracts 99(8)54963d, "Cellulose Decomposition in the Sintering of Fibers from Poly(tetrafluoroethylen) Dispersions" *Khim. Volokna* 3 33–34 1983.

Gusev, V.K. et al. Chemical Abstracts 96(10)70305j, "Two-–Component Acetate Threads" *Khim. Volokna* 6 31–32 1981.

Zakirov, I.Z. Chemical Abstracts 96(4)21192M, "Effect of Small Amounts of Polymeric Additives on Structural–Mechanical and Thermal Properties of Synthetic Fibers Spun By a Wet Method" *3–i Mezhdunar. Simpoz. po Khim. Voloknam. Kalinin. 1981, Kalinin* 5 105–110 1981.

Good Robert J., et al. *Surface and Colloid Science–Experimental Methods* II 31–91 1979.

Fedorova, R.G. et al. Chemical Abstracts 188(16)106639x, "Structural Thermal Stabilization of Fibers Based on Aromatic and Heterocyclic Polymer Blends" *Prepr.–Mezhdunar. Simp.Khim. Voloknam 2nd* 4 36–45 1977.

Geleji, Frigyes et al. Chemical Abstracts 82(14)87465v, "Bicomponent Fiberr Structures on Polypropylene Basis" *J. Polym. Sci., Polym. Symp.* 42, 713–716 Pt. 2 1973.

Whittington, Lloyd R. Whittington's Dictionary of Plastics p. 258 1968.

Database WPI Derwent Publications Ltd., Database WPI, EP 640474, (H. Utz), "Laminated Film Manufactured By Vacuum Deposition of Functional Layer Between Two Films".

Database WPI Derwent Publications Ltd., Database WPI, JP 6–212511 A, (Unitika Ltd.), "Biodegradable Staple Fiber Useful for Sanitary Napkin".

Database WPI Derwent Publications Ltd., Database WPI, JP 9–041220 A, (Unitika Ltd.), "Biodegradable Polyester Fiber".

Chemical Abstracts 114(22)209209s: abstract of laid open Japanese patent application JP 3040865.

Chemical Abstracts 119(12)119421d: abstract of laid open Japanese patent application JP 5093316.

Chemical Abstracts 119(12)119422e: abstract of laid open Japanese patent application JP 5093318.

Chemical Abstracts 119(24)252062d: abstract of laid open Japanese patent application JP 5163616.

Chemical Abstracts 120(8)79336s: abstract of laid open Japanese patent application JP 5093317.

Chemical Abstracts 122(2)12043s: abstract of laid open Japanese patent application JP 6212548.

Chemical Abstracts 122(2)12091f: abstract of laid open Japanese patent application JP 6248515.

Derwent World Patents Database, abstract of JP 06–248551 (Kuraray Co. Ltd), "Aliphatic Polyester Based Melt Blown Nonwoven Fabric".

Patent Abstracts of Japan, abstract of JP 08–188922 (Aikawa Toshio), "Conjugate Fiber and Fiber Sheet Using the Same".

Derwent World Patents Database, abstract of JP 04–335060 (Mitsui Toatsu Chem Inc (MITK)), "Thermoplastic and Decomposable Polymer Composition for Packaging".

* cited by examiner

METHODS FOR MAKING A THERMOPLASTIC COMPOSITION AND FIBERS INCLUDING SAME

CROSS-REFERENCE TO RELATED APPLICATIONS

This application is a application of U.S. patent application Ser. No. 09/436,682,filed Nov. 9, 1999, now U.S. Pat. No. 6,201,068 which is a continuation-in-part patent application of U.S. patent application Ser. No. 09/222,094, filed on Dec. 29, 1998,now U.S. Pat. No. 6,211,294, which is a divisional patent application of U.S. patent application Ser. No. 08/962,432, filed on Oct. 31, 1997,now U.S. Pat. No. 5,910,545, issued Jun. 8, 1999.

FIELD OF THE INVENTION

The present invention relates to a disposable Do absorbent product having a biodegradable nonwoven material having improved fluid management properties. The nonwoven material may be produced from polymer blends. These blends may include multicomponent fibers. These multicomponent fibers comprise an unreacted mixture of a poly(lactic acid) polymer, a polybutylene succinate polymer or a polybutylene succinate adipate polymer or a mixture of such polymers, and a wetting agent. The multicomponent fiber exhibits substantial biodegradable properties yet is easily processed. The disposable absorbent products may be used for the absorption of fluids such as body fluids.

BACKGROUND OF THE INVENTION

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover backsheet materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way. If the outer cover materials are made very thin in order to reduce the overall bulk of the disposable absorbent product so as to reduce the likelihood of blockage of a toilet or a sewage pipe, then the outer cover material typically will not exhibit sufficient strength to prevent tearing or ripping as the outer cover material is subjected to the stresses of normal use by a wearer.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that can be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting. Alternatively, the disposable absorbent product may be easily and efficiently disposed of to a liquid sewage system wherein the disposable absorbent product is capable of being degraded.

Although degradable monocomponent fibers are known, problems have been encountered with their use. In particular, known degradable fibers typically do not have good thermal dimensional stability such that the fibers usually undergo severe heat-shrinkage due to the polymer chain relaxation during downstream heat treatment processes such as thermal bonding or lamination.

For example, although fibers prepared from poly(lactic acid) polymer are known, problems have been encountered with their use. In particular, poly(lactic acid) polymers are known to have a relatively slow crystallization rate as compared to, for example, polyolefin polymers, thereby often resulting in poor processability of the aliphatic polyester polymers. In addition, the poly(lactic acid) polymers generally do not have good thermal dimensional-stability. The poly(lactic acid) polymers usually undergo severe heat-shrinkage due to the relaxation of the polymer chain during downstream heat treatment processes, such as thermal bonding and lamination, unless an extra step such as heat setting is taken. However, such a heat setting step generally limits the use of the fiber in in-situ nonwoven forming processes, such as spunbond and meltblown, where heat setting is very difficult to be accomplished.

Additionally, one of the more important components of many personal care articles is the body-side liner. The liner is usually comprised of a surfactant-treated polyolefin spunbond. For a spunbond to be implemented as a liner, it is desired that the material be wettable to promote intake of fluid insults. In addition to rapid intake, it is desired that the composite absorbent product keep the user's skin dry. In addition, it is desirable for the spunbond material to feel soft against the skin. The current spunbond diaper liner has a number of problems associated with it. First, it is comprised of polyolefinic materials and does not degrade. Due to the hydrophobic nature of these materials, the liner must be treated with a surfactant to make it wettable. Because there is no permanent anchoring of the surfactant to the polyolefin, it has a tendency to wash off during multiple insults, increasing intake times of the personal care products.

Accordingly, there is a need for a disposable absorbent product with improved fluid management properties such as faster intake times and improved skin dryness. Additionally there is a need for a disposable absorbent product that is biodegradable while also providing these improved fluid management properties.

SUMMARY OF THE INVENTION

It is therefore desired to provide a disposable absorbent product having improved fluid management properties.

It is also desired to provide a disposable absorbent product having faster intake times.

It is also desired to provide a disposable absorbent product having improved skin dryness.

It is also desired to provide a disposable absorbent product that is biodegradable while also providing improved fluid management properties.

It is also desired to provide a disposable absorbent product having a nonwoven material comprising a thermoplastic composition which exhibits desired processability, liquid wettability, and thermal dimensional-stability properties.

It is also desired to provide a disposable absorbent product having a nonwoven material comprising a thermoplastic composition which may be easily and efficiently formed into a fiber.

It is also desired to provide a disposable absorbent product that may be used for the absorption of fluids such as bodily fluids, yet which such disposable absorbent product comprises components that are readily degradable in the environment.

These desires are fulfilled by the present invention which provides a disposable absorbent product having a nonwoven material comprising a thermoplastic composition that is substantially biodegradable and yet which is easily prepared and readily processable into desired disposable absorbent products.

One aspect of the present invention concerns a disposable absorbent product having a thermoplastic composition that comprises a mixture of a first component, a second component, and a third component.

One embodiment of such a thermoplastic composition comprises an unreacted mixture of a poly(lactic acid) polymer; a polybutylene succinate polymer or a polybutylene succinate adipate polymer or a mixture of such polymers; and a wetting agent for the poly(lactic acid) polymer, the polybutylene succinate polymer or the polybutylene succinate adipate polymer or a mixture of such polymers.

In another aspect, the present invention concerns a multicomponent fiber that is substantially degradable and yet which is easily prepared and readily processable into the desired final disposable absorbent products.

One aspect of the present invention concerns a multicomponent fiber that comprises an unreacted mixture of a poly(lactic acid) polymer; a polybutylene succinate polymer or a polybutylene succinate adipate polymer or a mixture of such polymers; and a wetting agent for the aliphatic polyester polymer and the polybutylene succinate polymer or the polybutylene succinate adipate polymer or a mixture of such polymers.

In another aspect, the present invention concerns a nonwoven structure comprising the multicomponent fiber disclosed herein.

One embodiment of such a nonwoven structure is a frontsheet useful in a disposable absorbent product.

In another aspect, the present invention concerns a disposable absorbent product comprising the multicomponent fiber disclosed herein.

DETAILED DESCRIPTION OF INVENTION

The present invention is directed to a disposable absorbent product having a biodegradable nonwoven material which includes a thermoplastic composition comprising a first component, a second component, and a third component. As used herein, the term "thermoplastic" is meant to refer to a material that softens when exposed to heat and substantially returns to its original condition when cooled to room temperature.

It has been discovered that, by using an unreacted mixture of a poly(lactic acid) polymer, a polybutylene succinate polymer or a polybutylene succinate adipate polymer or a mixture of such polymers, and a wetting agent, a thermoplastic composition may be prepared wherein such thermoplastic composition is substantially degradable yet which thermoplastic composition is easily processed into fibers and nonwoven structures that exhibit effective fibrous mechanical properties.

The first component in the thermoplastic composition is poly(lactic acid) polymer. Poly(lactic acid) polymer is generally prepared by the polymerization of lactic acid. However, it will be recognized by one skilled in the art that a chemically equivalent material may also be prepared by the polymerization of lactide. As such, as used herein, the term "poly(lactic acid) polymer" is intended to represent the polymer that is prepared by either the polymerization of lactic acid or lactide.

Lactic acid and lactide are known to be asymmetrical molecules, having two optical isomers referred to, respectively, as the levorotatory (hereinafter referred to as "L") enantiomer and the dextrorotatory (hereinafter referred to as "D") enantiomer. As a result, by polymerizing a particular enantiomer or by using a mixture of the two enantiomers, it is possible to prepare different polymers that are chemically similar yet which have different properties. In particular, it has been found that by modifying the stereochemistry of a poly(lactic acid) polymer, it is possible to control, for example, the melting temperature, melt rheology, and crystallinity of the polymer. By being able to control such properties, it is possible to prepare a thermoplastic composition and a multicomponent fiber exhibiting desired melt strength, mechanical properties, softness, and processability properties so as to be able to make attenuated, heat-set, and crimped fibers.

Examples of poly(lactic acid) polymers that are suitable for use in the present invention include a variety of poly (lactic acid) polymers that are available from Chronopol Inc., Golden, Colorado.

It is generally desired that the poly(lactic acid) polymer be present in the thermoplastic composition in an amount effective to result in the thermoplastic composition exhibiting desired properties. The poly(lactic acid) polymer will be present in the thermoplastic composition in a weight amount that is greater than 0 but less than 100 weight percent, beneficially between about 5 weight percent to about 95 weight percent, suitably between about 10 weight percent to about 90 weight percent, and more suitably between about 15 weight percent to about 85 weight percent, wherein all weight percents are based on the total weight amount of the poly(lactic acid) polymer, the polybutylene succinate polymer or polybutylene succinate adipate polymer or a mixture of such polymers, and the wetting agent present in the thermoplastic composition. The compositional ratio of the three components in the thermoplastic composition is generally important to obtain the desired properties of the thermoplastic composition, such as wettability, biodegradability, thermal stability and processability.

The second component in the thermoplastic composition is a polybutylene succinate polymer, a polybutylene succinate adipate polymer, or a mixture of such polymers. A polybutylene succinate polymer is generally prepared by the condensation polymerization of a glycol and a dicarboxylic acid or an acid anhydride thereof. A polybutylene succinate polymer may either be a linear polymer or a long-chain branched polymer. A long-chain branched polybutylene succinate polymer is generally prepared by using an additional polyfunctional component selected from the group consisting of trifunctional or tetrafunctional polyols, oxycarboxylic acids, and polybasic carboxylic acids. Polybutylene succinate polymers are known in the art and are described, for example, in European Patent Application 0 569 153 A2 to Showa Highpolymer Co., Ltd., Tokyo, Japan. A polybutylene succinate adipate polymer is generally prepared by the polymerization of at least one alkyl glycol and more than one aliphatic multifunctional acid. Polybutylene succinate adipate polymers are also known in the art.

Examples of polybutylene succinate polymers and polybutylene succinate adipate polymers that are suitable for use in the present invention include a variety of polybutylene succinate polymers and polybutylene succinate adipate polymers that are available from Showa Highpolymer Co., Ltd., Tokyo,. Japan, under the designation Bionolle 1903 polybutylene succinate polymer, with long chain branches, or Bionolle 1020 polybutylene succinate polymer, which is an essentially linear polymer.

It is generally desired that the polybutylene succinate polymer, the polybutylene succinate adipate polymer, or a mixture of such polymers be present in the thermoplastic composition in an amount effective to result in the thermoplastic composition exhibiting desired properties. The polybutylene succinate polymer, the polybutylene succinate adipate polymer, or a mixture of such polymers will be present in the thermoplastic composition in a weight amount that is greater than 0 but less than 100 weight percent, beneficially between about 5 weight percent to about 95 weight percent, suitably between about 10 weight percent to about 90 weight percent, and more suitably between about 15 weight percent to about 85 weight percent, wherein all weight percents are based on the total weight amount of the poly(lactic acid) polymer; the polybutylene succinate polymer, the polybutylene succinate adipate polymer, or a mixture of such polymers; and the wetting agent present in the thermoplastic composition.

It is generally desired that the poly(lactic acid) polymer and the polybutylene succinate polymer and/or the polybutylene succinate adipate polymer exhibit a weight average molecular weight that is effective for the thermoplastic composition to exhibit desirable melt strength, fiber mechanical strength, and fiber spinning properties. In general, if the weight average molecular weight of a particular polymer is too high, this represents that the polymer chains are heavily entangled which may result in a thermoplastic composition comprising that polymer being difficult to process. Conversely, if the weight average molecular weight of a particular polymer is too low, this represents that the polymer chains are not entangled enough which may result in a thermoplastic composition comprising that polymer exhibiting a relatively weak melt strength, making high speed processing very difficult. Thus, poly(lactic acid) polymers, polybutylene succinate polymers, and/or polybutylene succinate adipate polymers suitable for use in the present invention respectively exhibit weight average molecular weights that are beneficially between about 10,000 to about 2,000,000, more beneficially between about 50,000 to about 400,000, and suitably between about 100,000 to about 300,000. The weight average molecular weight for polymers or polymer blends can be determined using a method as described in the Test Methods section herein.

It is also desired that the poly(lactic acid) polymer and the polybutylene succinate polymer and/or the polybutylene succinate adipate polymer exhibit a polydispersity index value that is effective for the thermoplastic composition to exhibit desirable melt strength, fiber mechanical strength, and fiber spinning properties. As used herein, "polydispersity index" is meant to represent the value obtained by dividing the weight average molecular weight of a polymer by the number average molecular weight of the polymer. In general, if the polydispersity index value of a particular polymer is too high, a thermoplastic composition comprising that polymer may be difficult to process due to inconsistent processing properties caused by polymer segments comprising low molecular weight polymers that have lower melt strength properties during spinning. Thus, it is desired that the poly(lactic acid) polymer, the polybutylene succinate polymer, and/or the polybutylene succinate adipate polymer respectively exhibit a polydispersity index value that is beneficially between about 1 to about 15, more beneficially between about 1 to about 4, and suitably between about 1 to about 3. The number average molecular weight for polymers or polymer blends can be determined using a method as described in the Test Methods section herein.

In the present invention, it is desired that the poly(lactic acid) polymer, the polybutylene succinate polymer, and the polybutylene succinate adipate polymer be biodegradable. As a result, the disposable absorbent product having the thermoplastic composition comprising these polymers will be substantially degradable when disposed of to the environment and exposed to air and/or water. As used herein, "biodegradable" is meant to represent that a material degrades from the action of naturally occurring microorganisms such as bacteria, fungi, and algae.

In the present invention, it is also desired that the poly (lactic acid) polymer, the polybutylene succinate polymer, and the polybutylene succinate adipate polymer be compostable. As a result, the disposable absorbent product having the thermoplastic composition comprising these polymers will be substantially compostable when disposed of to the environment and exposed to air and/or water. As used herein, "compostable" is meant to represent that the material is capable of undergoing biological decomposition in a compost site such that the material is not visually distinguishable and breaks down into carbon dioxide, water, inorganic compounds, and biomass, at a rate consistent with known compostable materials.

As used herein, the term "hydrophobic" refers to a material having a contact angle of water in air of at least 90 degrees. In contrast, as used herein, the term "hydrophilic" refers to a material having a contact angle of water in air of less than 90 degrees. For the purposes of this application, contact angle measurements are determined as set forth in the Test Methods section herein. The general subject of contact angles and the measurement thereof is well known in the art as, for example, in Robert J. Good and Robert J. Stromberg, Ed., in "Surface and Colloid Science—Experimental Methods", Vol. 11, (Plenum Press, 1979).

It is generally desired that the poly(lactic acid) polymer, the polybutylene succinate polymer, the polybutylene succinate adipate polymer, or a mixture of such polymers, be melt processable. It is therefore desired that the polymers used in the present invention exhibit a melt flow rate that is beneficially between about 1 gram per 10 minutes to about 600 grams per 10 minutes, suitably between about 5 grams per 10 minutes to about grams per 10 minutes, and more suitably between about 10 grams per 10 minutes to about 150 grams per 10 minutes. The melt flow rate of a material may be determined according to ASTM Test Method D1238-E, incorporated in its entirety herein by reference.

As used herein, the term "fiber" or "fibrous" is meant to refer to a material wherein the length to diameter ratio of such material is greater than about 10. Conversely, a "non-fiber" or "nonfibrous" material is meant to refer to a material wherein the length to diameter ratio of such material is about 10 or less.

Either separately or when mixed together, the poly(lactic acid) polymer and the polybutylene succinate polymer and/or the polybutylene succinate adipate polymer are generally hydrophobic. Since it is desired that the disposable absorbent products of the present invention prepared from the thermoplastic composition, generally be hydrophilic, it has been found that there is a need for the use of another component in the thermoplastic composition of the present invention in order to achieve the desired properties. Furthermore, it has been found desirable to improve the processability of the poly(lactic acid) polymer, and the polybutylene succinate polymer and/or the polybutylene succinate adipate, since such polymers are not chemically identical and are, therefore, somewhat incompatible with each other which negatively affects the processing of a mixture of such polymers. For example, the poly(lactic acid) polymer, the polybutylene succinate polymer, and/or the polybutylene succinate adipate polymer are sometimes difficult to effectively mix and prepare as an essentially homogeneous mixture on their own. As such, the present invention generally requires the use of a wetting agent that allows for the effective preparation and processing of the poly(lactic acid) polymer, the polybutylene succinate polymer, and/or the polybutylene succinate adipate polymer into a single thermoplastic composition.

Thus, the third component in the thermoplastic composition is a wetting agent for the poly(lactic acid) polymer and the polybutylene succinate polymer and/or the polybutylene succinate adipate polymer. Wetting agents suitable for use in the present invention will generally comprise a hydrophilic section which will generally be compatible to poly(lactic acid) polymer and the hydrophilic sections of polybutylene succinate polymer or polybutylene succinate adipate polymer and a hydrophobic section which will generally be compatible to the hydrophobic sections of polybutylene succinate polymer or polybutylene succinate adipate polymer. These hydrophilic and hydrophobic sections of the wetting agent will generally exist in separate blocks so that the overall wetting agent structure may be di-block or random block. It is generally desired that the wetting agent initially functions as a plasticizer and an agent to enhance cohesion between the different polymers in order to improve the preparation and processing of the thermoplastic composition. It is then generally desired that the wetting agent then serves as a surfactant in the nonwoven material processed from the thermoplastic composition by modifying the contact angle of water in air of the processed material. The hydrophobic portion of the wetting agent may be, but is not limited to, a polyolefin such as polyethylene or polypropylene. The hydrophilic portion of the wetting agent may contain ethylene oxide, ethoxylates, glycols, alcohols or any combinations thereof. Examples of suitable wetting agents include UNITHOX®480 and UNITHOX®750 ethoxylated alcohols, or UNICID® Acid Amide Ethoxylates, all available from Petrolite Corporation of Tulsa, Oklahoma.

It is generally desired that the wetting agent exhibit a weight average molecular weight that is effective for the thermoplastic composition to exhibit desirable melt strength, fiber mechanical strength, and fiber spinning properties. In general, if the weight average molecular weight of a wetting agent is too high, the wetting agent will not blend well with the other components in the thermoplastic composition because the wetting agent's viscosity will be so high that it lacks the mobility needed to blend. Conversely, if the weight average molecular weight of the wetting agent is too low, this represents that the wetting agent will generally not blend well with the other components and have such a low viscosity that it causes processing problems. Thus, wetting agents suitable for use in the present invention exhibit weight average molecular weights that are beneficially between about 1,000 to about 100,000, suitably between about 1,000 to about 50,000, and more suitably between about 1,000 to about 10,000. The weight average molecular weight for the poly(lactic acid) can be determined using a method as described in the Test Methods section herein.

It is generally desired that the wetting agent exhibit an effective hydrophilic-lipophilic balance ratio (HLB ratio). The HLB ratio of a material describes the relative ratio of the hydrophilicity of the material. The HLB ratio is calculated as the weight average molecular weight of the hydrophilic portion divided by the total weight average molecular weight of the material, which value is then multiplied by 20. If the HLB ratio value is too low, the wetting agent will generally not provide the desired improvement in hydrophilicity. Conversely, if the HLB ratio value is too high, the wetting agent will not blend into the thermoplastic composition because of chemical incompatibility and differences in viscosities with the other components. Thus, wetting agents useful in the present invention exhibit HLB ratio values that are beneficially between about 10 to about 40, suitably between about 10 to about 20, and more suitably between about 12 to about 16.

It is generally desired that the wetting agent be present in the thermoplastic composition in an amount effective to result in the thermoplastic composition exhibiting desired properties such as desirable heat shrinkage and desirable contact angle values. In general, a minimal amount of the wetting agent will be needed to achieve an effective blending and processing with the other components in the thermoplastic composition. In general, too much of the compatibilizer may lead to processing problems of the thermoplastic composition or to a final thermoplastic composition that does not exhibit desired properties such as desired advancing and receding contact angle values. The wetting agent will be present in the thermoplastic composition in a weight amount that is greater than 0 to about 15 weight percent, beneficially between about 0.5 weight percent to about 15 weight percent, more beneficially between about 1 weight percent to about 13 weight percent, suitably between about 1 weight percent to about 10 weight percent, and more suitably between about 1 weight percent to about 5 weight percent, wherein all weight percents are based on the total weight amount of the poly(lactic acid) polymer; the polybutylene succinate polymer, the polybutylene succinate adipate polymer, or a mixture of such polymers; and the wetting agent present in the thermoplastic composition.

While the principal components of the thermoplastic composition used in the present invention have been described in the foregoing, such thermoplastic composition is not limited thereto and can include other components not adversely effecting the desired properties of the thermoplastic composition. Exemplary materials which could be used as additional components would include, without limitation, pigments, antioxidants, stabilizers, surfactants, waxes, flow promoters, solid solvents, plasticizers, nucleating agents, particulates, and other materials added to enhance the processability of the thermoplastic composition. If such additional components are included in a thermoplastic composition, it is generally desired that such additional components be used in an amount that is beneficially less than about 10 weight percent, more beneficially less than about 5 weight percent, and suitably less than about 1 weight percent, wherein all weight percents are based on the total weight amount of the poly(lactic acid) polymer; the polybutylene succinate polymer, the polybutylene succinate adipate polymer, or a mixture of such polymers; and the wetting agent present in the thermoplastic composition.

The thermoplastic composition used in the present invention is generally the resulting morphology of a mixture of the poly(lactic acid) polymer; the polybutylene succinate polymer, the polybutylene succinate adipate polymer, or a mixture of such polymers; the wetting agent, and, optionally, any additional components. In order to achieve the desired properties for the thermoplastic composition, it is desirable that the poly(lactic acid) polymer; the polybutylene succinate polymer, the polybutylene succinate adipate polymer, or a mixture of such polymers; and the wetting agent remain substantially unreacted with each other. As such, each of the poly(lactic acid) polymer; the polybutylene succinate polymer, the polybutylene succinate adipate polymer, or a mixture of such polymers; and the wetting agent remain distinct components of the thermoplastic composition.

Each of the poly(lactic acid) polymer and the polybutylene succinate polymer, the polybutylene succinate adipate polymer, or a mixture of such polymers will generally form separate regions or domains within a prepared mixture forming the thermoplastic composition. However, depending on the relative amounts that are used of each of the poly(lactic acid) polymer and the polybutylene succinate polymer, the polybutylene succinate adipate polymer, or a mixture of such polymers, an essentially continuous phase may be formed from the polymer that is present in the thermoplastic composition in a relatively greater amount. In contrast, the polymer that is present in the thermoplastic composition in a relatively lesser amount may form an essentially discontinuous phase, forming separate regions or domains within the continuous phase of the more prevalent polymer wherein the more prevalent polymer continuous phase substantially encases the less prevalent polymer within its structure. As used herein, the term "encase", and related terms, are intended to mean that the more prevalent polymer continuous phase substantially encloses or surrounds the less prevalent polymer's separate regions or domains.

In one embodiment of a thermoplastic composition or a multicomponent fiber used in the present invention, it is desired that the poly(lactic acid) polymer form an essentially continuous phase and that the polybutylene succinate polymer, the polybutylene succinate adipate polymer, or a mixture of such polymers form an essentially discontinuous phase, wherein the poly(lactic acid) polymer substantially encases regions or domains of the polybutylene succinate polymer, the polybutylene succinate adipate polymer, or a mixture of such polymers. In such an embodiment, it is desired that the poly(lactic acid) polymer is present in the thermoplastic composition or multicomponent fiber in a weight amount that is between about 75 weight percent to about 90 weight percent and that the polybutylene succinate polymer, the polybutylene succinate adipate polymer, or a mixture of such polymers is present in the thermoplastic composition or multicomponent fiber in a weight amount that is between about 5 weight percent to about 20 weight percent, wherein all weight percents are based on the total weight amount of the poly(lactic acid) polymer, the polybutylene succinate polymer or polybutylene succinate adipate polymer or a mixture of such polymers, and the wetting agent present in the thermoplastic composition or the multicomponent fiber.

In one embodiment of the present invention, after dry mixing together the poly(lactic acid) polymer; the polybutylene succinate polymer, the polybutylene succinate adipate polymer, or a mixture of such polymers; and the wetting agent to form a thermoplastic composition dry mixture, such thermoplastic composition dry mixture is beneficially agitated, stirred, or otherwise blended to effectively uniformly mix the poly(lactic acid) polymer; the polybutylene succinate polymer, the polybutylene succinate adipate polymer, or a mixture of such polymers; and the wetting agent such that an essentially homogeneous dry mixture is formed. The dry mixture may then be melt blended in, for example, an extruder, to effectively uniformly mix the poly(lactic acid) polymer; the polybutylene succinate polymer, the polybutylene succinate adipate polymer, or a mixture of such polymers; and the wetting agent such that an essentially homogeneous melted mixture is formed. The essentially homogeneous melted mixture may then be cooled and pelletized. Alternatively, the essentially homogeneous melted mixture may be sent directly to a spin pack or other equipment for forming fibers or a nonwoven structure.

Alternative methods of mixing together the components of the present invention include first mixing together the poly(lactic acid) polymer and the polybutylene succinate polymer, the polybutylene succinate adipate polymer, or a mixture of such polymers and then adding the wetting agent to such a mixture in, for example, an extruder being used to mix the components together. In addition, it is also possible to initially melt mix all of the components together at the same time. Other methods of mixing together the components of the present invention are also possible and will be easily recognized by one skilled in the art.

The present invention also utilizes a multicomponent fiber which is prepared from the thermoplastic composition of the present invention. For purposes of illustration only, the present invention will generally be described in terms of a multicomponent fiber comprising only three components. However, it should be understood that the scope of the present invention is meant to include fibers with three or more components.

When the thermoplastic composition is formed into a multicomponent fiber, an exposed surface on at least a portion of the multicomponent fiber will typically be formed from the more prevalent polymer present in the multicomponent fiber. Such an exposed surface on at least a portion of the multicomponent fiber which will generally permit thermal bonding of the multicomponent fiber to other fibers which may be the same or different from the multicomponent fiber of the present invention. As a result, the multicomponent fiber can then be used to form thermally bonded fibrous nonwoven structures such as a nonwoven web.

Typical conditions for thermally processing the various components include using a shear rate that is beneficially between about 100 seconds-1 to about 50000 seconds-1, more beneficially between about 500 seconds-1 to about 5000 seconds-1, suitably between about 1000 seconds-1 to about 3000 seconds-1, and most suitably at about 1000 seconds-1. Typical conditions for thermally processing the components also include using a temperature that is beneficially between about 100° C. to about 500° C., more beneficially between about 125° C. to about 300° C., and suitably between about 150° C. to about 250° C.

Methods for making multicomponent fibers are well known and need not be described here in detail. The melt spinning of polymers includes the production of continuous filament, such as spunbond or meltblown, and non-continuous filament, such as staple and short-cut fibers. To form a spunbond or meltblown fiber, generally, a thermoplastic composition is extruded and fed to a distribution system where the thermoplastic composition is introduced into a spinneret plate. The spun fiber is then cooled, solidified, and drawn by an aerodynamic system, to be formed into a conventional nonwoven. Meanwhile, to produce short-cut or staple fiber rather than being directly formed into a nonwoven structure the spun fiber is cooled, solidified, and drawn, generally by a mechanical rolls system, to an intermediate filament diameter and collected. Subsequently, the fiber may be "cold drawn" at a temperature below its softening temperature, to the desired finished fiber diameter and crimped or texturized and cut into a desirable fiber length.

The process of cooling an extruded thermoplastic composition to ambient temperature is usually achieved by blowing ambient or sub-ambient temperature air over the extruded thermoplastic composition. It can be referred to as quenching or super-cooling because the change in temperature is usually greater than 100∞ C. and most often greater than 150∞ C. over a relatively short time frame, such as in seconds.

Multicomponent fibers can be cut into relatively short lengths, such as staple fibers which generally have lengths in the range of about 25 to about 50 millimeters and short-cut fibers which are even shorter and generally have lengths less than about 18 millimeters. See, for example, U.S. Pat. No. 4,789,592 to Taniguchi et al, and U.S. Pat. No. 5,336,552 to Strack et al., both of which are incorporated herein by reference in their entirety.

The resultant multicomponent fibers are desired to exhibit an improvement in hydrophilicity, evidenced by a decrease in the contact angle of water in air. The contact angle of water in air of a fiber sample can be measured as either an advancing or a receding contact angle value because of the nature of the testing procedure. The advancing contact angle measures a material's initial response to a liquid, such as water. The receding contact angle gives a measure of how a material will perform over the duration of a first insult, or exposure to liquid, as well as over following insults. A lower receding contact angle means that the material is becoming more hydrophilic during the liquid exposure and will generally then be able to transport liquids more consistently. Both the advancing and receding contact angle data is desirably used to establish the highly hydrophilic nature of a multicomponent fiber.

Thus, in one embodiment of the present invention, it is desired that the multicomponent fiber exhibits an Advancing Contact Angle value that is beneficially less than about 80 degrees, more beneficially less than about 75 degrees, suitably less than about 70 degrees, more suitably less than about 60 degrees, and most suitably less than about 50 degrees, wherein the Advancing Contact Angle value is determined by the method that is described in the Test Methods section herein.

In another embodiment of the present invention, it is desired that the multicomponent fiber exhibits a Receding Contact Angle value that is beneficially less than about 60 degrees, more beneficially less than about 55 degrees, suitably less than about 50 degrees, more suitably less than about 45 degrees, and most suitably less than about 40 degrees, wherein the Receding Contact Angle value is determined by the method that is described in the Test Methods section herein.

In another embodiment of the present invention, it is desired that the difference between the Advancing Contact Angle value and the Receding Contact Angle value, commonly known as the contact angle hysteresis, be as small as possible. As such, it is desired that the multicomponent fiber exhibits a difference between the Advancing Contact Angle value and the Receding Contact Angle value that is beneficially less than about 30 degrees, more beneficially less than about 25 degrees, suitably less than about 20 degrees, and more suitably less than about 10 degrees.

Typical poly(lactic acid) polymer materials often undergo heat shrinkage during downstream thermal processing. The heat-shrinkage mainly occurs due to the thermally-induced chain relaxation of the polymer segments in the amorphous phase and incomplete crystalline phase. To overcome this problem, it is generally desirable to maximize the crystallization of the poly(lactic acid) polymer material before the bonding stage so that the thermal energy goes directly to melting rather than to allow for chain relaxation and reordering of the incomplete crystalline structure. The typical solution to this problem is to subject the material to a heat-setting treatment. As such, when prepared materials, such as fibers, are subjected to heat-setting As upon reaching a bonding roll, the fibers won't substantially shrink because such fibers are already fully or highly oriented. The present invention alleviates the need for this additional processing step because of the morphology of the multicomponent fiber. In general, the addition of the polybutylene succinate polymer, the polybutylene succinate adipate polymer, or a mixture of such polymers, and the wetting agent decrease the heat shrinkage of a multicomponent fiber as compared to a fiber that is prepared from only poly(lactic acid) polymer.

In one embodiment of the present invention, it is desired that the disposable absorbent product utilize a thermoplastic composition or a multicomponent fiber which exhibits an amount of shrinking, at a temperature of about 90° C., that is beneficially less than about 15 percent, more beneficially less than about 10 percent, and suitably less than about 5 percent, wherein the amount of shrinking is based upon the difference between the initial and final lengths of the fiber divided by the initial length of the fiber multiplied by 100. The method by which the amount of shrinking that a fiber exhibits may be determined is included in the Test Methods section herein.

In one embodiment of the present invention, it is desired that the multicomponent fiber exhibit an amount of shrinking, suitably less than about 5 percent at a temperature of about 90° C., that results in a nonwoven structure formed from the multicomponent fiber to exhibit a quilting or waviness effect that increases the surface area of the nonwoven structure since the shrinking of the multicomponent fibers causes the nonwoven structure to exhibit a three dimensional topography. Such a quilting or waviness effect of the nonwoven structure has been found to improve the softness and z-directional transport of a liquid within a disposable absorbent product.

It is generally desired that multicomponent fibers also exhibit desired mechanical strength properties, such as a break stress value as well as a modulus value, such that the nonwoven materials maintain their integrity during use. In one embodiment of the present invention, it is desired that a multicomponent fiber, prepared from the thermoplastic composition previously described, exhibits an improved break stress value as well as an improved modulus value as compared to a fiber that is prepared solely from poly(lactic acid) polymer. In one embodiment of the present invention, it is desired that the multicomponent fiber also exhibits a break stress value that is at least twice the break stress value exhibited by an otherwise identical fiber that is prepared solely from the poly(lactic acid) polymer used to prepare the multicomponent fiber.

In one embodiment of the present invention, it is desired that the multicomponent fiber exhibit a break stress value that is greater than about 10 MPa, beneficially greater than about 15 MPa, suitably greater than about 20 MPa, and up to about 100 MPa.

In another embodiment of the present invention, it is desired that the multicomponent fiber exhibit a modulus value that is less than about 150 MPa, beneficially less than about 125 MPa, and suitably less than about 100 MPa.

The biodegradable nonwoven materials described herein are suited for use in disposable products including disposable absorbent products such as diapers, adult incontinent products, and bed pads; in catamenial devices such as sanitary napkins, and tampons; and other absorbent products such as wipes, bibs, wound dressings, and surgical capes or drapes. Accordingly, in another aspect, the present invention relates to a disposable absorbent product comprising the multicomponent fibers.

In one embodiment of the present invention, the multicomponent fibers are formed into a fibrous matrix for incorporation into a disposable absorbent product. A fibrous matrix may take the form of, for example, a fibrous nonwoven web. Fibrous nonwoven webs may be made completely from the multicomponent fibers of the present invention or they may be blended with other fibers. The length of the fibers used may depend on the particular end use contemplated. Where the fibers are to be degraded in water as, for example, in a toilet, it is advantageous if the lengths are maintained at or below about 15 millimeters.

In one embodiment of the present invention, a disposable absorbent product is provided, which disposable absorbent product generally comprises a composite structure including a liquid-permeable topsheet, a fluid acquisition layer, an absorbent structure, and a liquid-impermeable backsheet, wherein at least one of the liquid-permeable topsheet, the fluid acquisition layer, or the liquid-impermeable backsheet comprises the nonwoven material of the present invention. In some instances, it may be beneficial for all three of the topsheet, the fluid acquisition layer, and the backsheet to comprise the nonwoven material of the present invention.

In another embodiment, the disposable absorbent product may comprise generally a composite structure including a liquid-permeable topsheet, an absorbent structure, and a liquid-impermeable backsheet, wherein at least one of the liquid-permeable topsheet or the liquid-impermeable backsheet comprises the nonwoven material of the present invention.

In another embodiment of the present invention, the nonwoven material may be prepared on a spunbond line. Resin pellets comprising the thermoplastic materials previously described are formed and predried. Then, they are fed to a single extruder. The fibers may be drawn through a fiber draw unit (FDU) or air-drawing unit onto a forming wire and thermally bonded. However, other methods and preparation techniques may also be used.

Exemplary disposable absorbent products are generally described in U.S. Pat. No. 4,710,187; U.S. Pat. No. 4,762,521; U.S. Pat. No. 4,770,656; and U.S. Pat. No. 4,798,603; which references are incorporated herein by reference.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

TEST METHODS

Melting Temperature

The melting temperature of a material was determined using differential scanning calorimetry. A differential scanning calorimeter, under the designation Thermal Analyst 2910 Differential Scanning Calorimeter, which was outfitted with a liquid nitrogen cooling accessory and used in combination with Thermal Analyst 2200 analysis software (version 8.10) program, both available from T.A. Instruments Inc. of New Castle, Delaware, was used for the determination of melting temperatures.

The material samples tested were either in the form of fibers or resin pellets. It was preferred to not handle the material samples directly, but rather to use tweezers and other tools, so as not to introduce anything that would produce erroneous results. The material samples were cut, in the case of fibers, or placed, in the case of resin pellets, into an aluminum pan and weighed to an accuracy of 0.01 mg on an analytical balance. If needed, a lid was crimped over the material sample onto the pan.

The differential scanning calorimeter was calibrated using an indium metal standard and a baseline correction performed, as described in the manual for the differential scanning calorimeter. A material sample was placed into the test chamber of the differential scanning calorimeter for testing and an empty pan is used as a reference. All testing was run with a 55 cubic centimeter/minute nitrogen (industrial grade) purge on the test chamber. The heating and cooling program was a 2 cycle test that begins with equilibration of the chamber to −40° C., followed by a heating cycle of 20° C./minute to 200° C., followed by a cooling cycle at 20° C./minute to−40° C., and then another heating cycle of 20° C./mninute to 200° C.

The results were evaluated using the analysis software program wherein the glass transition temperature (Tg) of inflection, endothermic and exothermic peaks were identified and quantified. The glass transition temperature was identified as the area on the line where a distinct change in slope occurs and then the melting temperature is determined using an automatic inflection calculation.

Apparent Viscosity

A capillary rheometer, under the designation Göttfert Rheograph 2003 capillary rheometer, which was used in combination with WinRHEO (version 2.31) analysis software, both available from Göttfert Company of Rock Hill, S.C., was used to evaluate the apparent viscosity Theological properties of material samples. The capillary rheometer setup included a 2000 bar pressure transducer and a 30 mm length/30 mm active length/1 mm diameter/0 mm height/180° run in angle, round hole capillary die.

If the material sample being tested demonstrated or was known to have water sensitivity, the material sample was dried in a vacuum oven above its glass transition temperature, i.e. above 55 or 60° C. for poly(lactic acid) materials, under a vacuum of at least 15 inches of mercury with a nitrogen gas purge of at least 30 standard cubic feet per hour for at least 16 hours.

Once the instrument was warmed up and the pressure transducer was calibrated, the material sample was loaded incrementally into the column, packing resin into the column with a ramrod each time to ensure a consistent melt during testing. After material sample loading, a 2 minute melt time preceded each test to allow the material sample to completely melt at the test temperature. The capillary rheometer took data points automatically and determined the apparent viscosity (in Pascalûsecond) at 7 apparent shear rates (in second-1): 50, 100, 200, 500, 1000, 2000, and 5000. When examining the resultant curve it was important that the curve be relatively smooth. If there were significant deviations from a general curve from one point to another, possibly due to air in the column, the test run was repeated to confirm the results.

The resultant rheology curve of apparent shear rate versus apparent viscosity gives an indication of how the material sample will run at that temperature in an extrusion process. The apparent viscosity values at a shear rate of at least 1000 second-i are of specific interest because these are the typical conditions found in commercial fiber spinning extruders.

Molecular Weight

A gas permeation chromatography (GPC) method was used to determine the molecular weight distribution of samples, such as of poly(lactic acid) whose weight average molecular weight (Mw) is between about 800 to about 400,000.

The GPC was set up with two PL gel Mixed K linear 5 micron, 7.5×300 millimeter analytical columns in series. The column and detector temperatures were 30° C. The mobile phase was high-performance liquid chromatography (HPLC) grade tetrahydrofuran (THF). The pump rate was 0.8 milliliter per minute with an injection volume of 25 microliters. Total run time was 30 minutes. It is important to note that new analytical columns must be installed about every 4 months, a new guard column about every month, and a new in-line filter about every month.

Standards of polystyrene polymers, obtained from Aldrich Chemical Co., were mixed into a solvent of dichloromethane (DCM):THF (10:90), both HPLC grade, to obtain 1 mg/mL concentrations. Multiple polystyrene standards could be combined in one standard solution provided that their peaks do not overlap when chromatographed. A range of standards of about 687 to 400,000 molecular weight were prepared. Examples of standard mixtures with Aldrich polystyrenes of varying weight average molecular weights include: Standard 1 (401,340; 32,660; 2,727), Standard 2 (45,730; 4,075), Standard 3 (95,800; 12,860) and Standard 4 (184,200; 24,150; 687).

Next, the stock check standard was prepared. First, 10 g of a 200,000 molecular weight poly(lactic acid) standard, Catalog#19245 obtained from Polysciences Inc., was dissolved to 100 mi of HPLC grade DCM in a glass jar with a lined lid using an orbital shaker (at least 30 minutes). Next, the mixture was poured out onto a clean, dry, glass plate and the solvent allowed to evaporate, then placed in a 35° C. preheated vacuum oven and dried for about 14 hours under a vacuum of 25mm of mercury. Next, the poly(lactic acid) was removed from the oven and the film cut into small strips. Immediately, the samples were ground using a grinding mill (with a 10 mesh screen) taking care not to add too much sample and causing the grinder to freeze up. A few grams of the ground sample were stored in a dry glass jar in a dessicator, while the remainder of the sample can be stored in the freezer in a similar type jar.

It was important to prepare a new check standard prior to the beginning of each new sequence and, because the molecular weight is greatly affected by sample concentration, great care should be taken in its weighing and preparation. To prepare the check standard, 0.0800 g ±0.0025 g of 200,000 weight average molecular weight poly(lactic acid) reference standard was weighed out into a clean dry scintillation vial. Then, using a volumetric pipette or dedicated repipet, 2 ml of DCM was added to the vial and the cap screwed on tightly. The sample was allowed to dissolve completely. The sample was swirled on an orbital shaker, such as a Thermolyne Roto Mix (type 51300) or similar mixer, if necessary. To evaluate whether was it dissolved, the vial was held up to the light at a 45 angle. The vial was turned slowly and the liquid watched as it flowed down the glass. If the bottom of the vial did not appear smooth, the sample was not completely dissolved. It may take the sample several hours to dissolve. Once dissolved, 18 ml of THF was added using a volumetric pipette or dedicated repipet, the vial capped tightly and mix.

Sample preparations began by weighing 0.0800 g ±0.0025 g of the sample into a clean, dry scintillation vial (great care should also be taken in its weighing and preparation). 2 ml of DCM was added to the vial with a volumetric pipette or dedicated repipette and the cap screwed on tightly. The sample was allowed to dissolve completely using the same technique described in the check standard preparation above. Then 18 ml of THF was added using a volumetric pipette or dedicated repipette, the vial capped tightly and mixed.

The evaluation was begun by making a test injection of a standard preparation to test the system equilibration. Once equilibration was confirmed the standard preparations were injected. After those were run, first the check standard preparation was injected and then the sample preparations. The check standard preparation was injected after every 7 sample injections and at the end of testing. Be careful not to take any more than two injections from any one vial, and those two injections must be made within 4.5 hours of each other.

There are 4 quality control parameters to assess the results. First, the correlation coefficient of the fourth order regression calculated for each standard should be not less than 0.950 and not more than 1.050. Second, the relative standard deviation of all the weight average molecular weights of the check standard preparations should not be more than 5.0 percent. Third, the average of the weight average molecular weights of the check standard preparation injections should be within 10 percent of the weight average molecular weight on the first check standard preparation injection. Lastly, record the lactide response for the 200 microgram per milliliter (mg/mL) standard injection on a SQC data chart. Using the chart's control lines, the response must be within the defined SQC parameters.

Calculate the Molecular statistics based on the calibration curve generated from the polystyrene standard preparations and constants for poly(lactic acid) and polystyrene in THF at 30° C. Those are: Polystyrene (K=14.1*105 alpha=0.700) and poly(lactic acid) (K=54.9*105, alpha=0.639).

Heat Shrinkage of Fibers

The required equipment for the determination of heat shrinkage include: a convection oven (Thelco model 160DM laboratory oven, available from Precision and Scientific Inc., of Chicago, Illinois), 0.5 g (+/−0.06 g) sinker weights, 1 inch binder clips, masking tape, graph paper with at least 1 inch squares, foam posterboard (11 by 14 inches) or equivalent substrate to attach the graph paper and samples to. The convection oven should be capable of a temperature of about 100° C.

Fiber samples are melt spun at their respective spinning conditions. In general, a 30 filament bundle is preferred and mechanically drawn to obtain fibers with a jetstretch ratio of beneficially 224 or higher. Only fibers of the same jetstretch. ratio can be compared to one another in regards to their heat shrinkage. The jetstretch ratio of a fiber is the ratio of the speed of the drawdown roll divided by the linear extrusion rate (distance/time) of the melted polymer exiting the spinneret. The spun fiber is usually collected onto a bobbin using a winder. The collected fiber bundle was separated into 30 filaments, if a 30 filament bundle has not already been obtained, and cut into 9 inch lengths.

The graph paper was taped onto the posterboard where one edge of the graph paper was matched with the edge of the posterboard. One end of the fiber bundle was taped, no more than the end 1 inch. The taped end was clipped to the posterboard at the edge where the graph paper was matched up such that the edge of the clip rests over one of the horizontal lines on the graph paper while holding the fiber bundle in place (the taped end should be barely visible as it is secured under the clip). The other end of the bundle was pulled taught and lined up parallel to the vertical lines on the graph paper. Next, at 7 inches down from the point where the clip is binding the fiber, the 0.5 g sinker was pinched around the fiber bundle. The attachment process was repeated for each replicate. Usually, 3 replicates could be attached at one time. Marks could be made on the graph paper to indicate the initial positions of the sinkers. The samples were placed into the oven at a temperature of about 100° C. such that the samples hung vertically and did not touch the posterboard. At time intervals of 5, 10 and 15 minutes quickly the new location of the sinkers was marked on the graph paper and samples returned to the oven.

After the testing was complete, the posterboard was removed and the distances between the origin (where the clip held the fibers) and the marks at 5, 10 and 15 minutes were measured with a ruler graduated to 1/16 inch. Three replicates per sample is recommended. Calculate averages, standard deviations and percent shrinkage. The percent shrinkage is calculated as (initial length—measured length) divided by the initial length and multiplied by 100. As reported in the examples herein and as used throughout the claims, the Heat Shrinkage value represents the amount of heat shrinkage that a fiber sample exhibits at a temperature of about 100° C. for a time period of about 15 minutes, as determined according to the preceding test method.

Contact Angle

The equipment includes a DCA-322 Dynamic Contact Angle Analyzer and WinDCA (version 1.02) software, both available from ATI-CAHN Instruments, Inc., of Madison, Wis. Testing was done on the "A" loop with a balance stirrup attached. Calibrations should be done monthly on the motor and daily on the balance (100 mg mass used) as indicated in the manual. Thermoplastic compositions were spun into fibers and the freefall sample (jetstretch of 0) was used for the determination of contact angle. Care should be taken throughout fiber preparation to minimize fiber exposure to handling to ensure that contamination is kept to a minimum. The fiber sample was attached to the wire hanger with scotch tape such that 2–3 cm of fiber extended beyond the end of the hanger. Then the fiber sample was cut with a razor so that approximately 1.5 cm was extending beyond the end of the hanger. An optical microscope was used to determine the average diameter (3 to 4 measurements) along the fiber.

The sample on the wire hanger was suspended from the balance stirrup on loop "A". The immersion liquid was distilled water and it was changed for each specimen. The specimen parameters were entered (i.e. fiber diameter) and the test started. The stage advanced at 151.75 microns/second until it detected the Zero Depth of Immersion when the fiber contacted the surface of the distilled water. From the Zero Depth of Immersion, the fiber advanced into the water for 1 cm, dwelled for 0 seconds and then immediately receded 1 cm. The auto-analysis of the contact angle done by the software determined the advancing and receding contact angles of the fiber sample based on standard calculations identified in the manual. Contact angles of 0 or <0 indicate that the sample had become totally wettable. Five replicates for each sample were tested and a statistical analysis for mean, standard deviation, and coefficient of variation percent was calculated. As reported in the examples herein and as used throughout the claims, the Advancing Contact Angle value represents the advancing contact angle of distilled water on a fiber sample determined according to the preceding test method. Similarly, as reported in the examples herein and as used throughout the claims, the Receding Contact Angle value represents the receding contact angle of distilled water on a fiber sample determined according to the preceding test method.

Fluid-Intake and Flowback Evaluation (FIFE)

Fluid-Intake and Flowback Evaluation (FIFE) testing was used to determine the absorbency time and flowback of a personal care product. A Master-Flex Digi-Staltic Automatic Dispensing system was supplied with saline colored with a small amount of FD&C blue dye, set to provide 80 mL insults, and dispensed several times to eliminate any air bubbles. The product samples, infant care diapers, were prepared without elastics so that they would easily lie flat. Two 3.5 inch by 12 inch blotter paper samples were weighed. These papers were placed on the FIFE board, a simple board with a 3 inch by 6 inch raised platform in the middle. The blotter papers were aligned so that they ran lengthwise along either side of the raised platform. The diaper was then aligned so that the area to be insulted was carefully centered on the raised platform, with the topsheet facing up, such that there were no visible wrinkles in the nonwoven topsheet. The second FIFE board was then placed on top of the product. This apparatus consists of a flat board that was intersected by a hollow cylinder, protruding only from the top side of the board. The circular region created where the cylinder intersected the flat plane of the board was hollow. The inner diameter of the cylinder was 5.1 centimeters. A funnel with an inner diameter of 7 millimeters at the short end was placed in the cylinder. The fluid was then dispensed by the pump directly into the funnel. The intake time was recorded by stopwatch from the time the fluid hit the funnel to the moment no fluid was visible on the specimen surface. The blotter papers were checked for product leakage and if any occurred the weight of the blotter papers would have been measured to determine the quantity of fluid that leaked. In the described testing, no leakage occurred. Approximately one minute elapsed before the second insult was applied in the same manner. Again a third insult was applied and timed in the same manner. If desired a procedure may then follow to determine the amount of fluid flowing back when the product is under pressure. In this case, only the intake rates were recorded.

TransEpidermal Water Loss (TEWL)

TransEpidermal Water Loss (TEWL) armband testing was used to measure changes in skin hydration as a result of product use. A lower evaporation value, as measured by a Servo Med Evaporimeter, is indicative of a product that promotes skindryness. This test actually reports a difference in evaporation values. A measurement of moisture evaporation rate is taken prior to the test and then immediately following. The difference in these numbers provides the TEWL value as reported in the results. A lower TEWL value implies that a product provides better breathability to the skin.

Product, in this case infant care diapers, was prepared by hand without any elastics or ears. The basic structure of the diaper was the same, but one control diaper consisted entirely of standard materials and the other had all standard materials except for the topsheet, which was comprised of the biodegradable nonwoven. The target area for the insults was drawn in permanent marker on the outside of the product. All testing occurred in a controlled environment of 72±4F with a relative humidity of 40±5%. The subjects were adult women who were carefully selected to insure that they had no conditions that might potentially alter the results of such a test.

Subjects relaxed in a controlled environment until a stable baseline reading of less than 10 g2/m/hr is obtained with the Servo Med Evaporimeter. These measurements were performed on the inner forearm of the subjects. Masterflex Digi-Staltic batch/dispense pump was used with silicone tubing in the pump head, which was connected to neoprene tubing for dispensing, by barb fittings. The end of the neoprene dispensing tube was placed on the forearm of a subject and the product applied to the forearm with the target insult area directly on top of the tube opening. The product is secured with tape that was wrapped around the diaper and did not contact the skin. The diaper was then loaded with three insults of 60 mL of saline at 45 second intervals and the tube removed. The product was further secured with a stretchable net and the subject required to sit for one hour. After 60 minutes of wear, the product was removed and the Evaporimeter was then used to obtain readings every second for two minutes in the same area on the forearm as the baseline readings were taken. The reported result is the difference between the one-hour and baseline readings.

EXAMPLES

Various materials were used as components to form thermoplastic compositions and multicomponent fibers in the following Examples. The designation and various properties of these materials are listed in Table 1.

Heplon A10005 poly(lactic acid) (PLA) polymers were obtained from Chronopol Inc., Golden, Colo.

A polybutylene succinate (PBS), available from Showa Highpolymer Co., Ltd., Tokyo, Japan, under the designation Bionolle 1020 polybutylene succinate, was obtained.

A polybutylene succinate (PBS) with long chain branching, available from Showa Highpolymer Co., Ltd., Tokyo, Japan, under the designation Bionolle 1903 polybutylene succinate, was obtained.

The wetting agent used throughout the examples was obtained from Petrolite Corporation of Tulsa, Oklahoma, under the designation UNITHOX®480 ethoxylated alcohol, which exhibited a number average molecular weight of about 2250, an ethoxylate percent of about 80 weight percent, and an HLB value of about 16.

TABLE 1

| Material Designation | L:D Ratio | Melting Temp. (° C.) | Weight Average Molecular Weight | Number Average Molecular Weight | Polydispersity Index | Residual Lactic Acid Monomer |
|---|---|---|---|---|---|---|
| PLA Sample 1 | 100:0 | 175 | 187,000 | 118,000 | 1.58 | <1% |
| PLA Sample 2 | 95:5 | 140–145 | 190,000 | 108,000 | 1.76 | <3% |
| Bionolle 1020 | N/A | 95 | 40,000 to 1,000,000 | 20,000 to 300,000 | ~2 to ~3.3 | N/A |
| Bionolle 1903 | N/A | 120 | 40,000 to 1,000,000 | 20,000 to 300,000 | ~2 to ~3.3 | N/A |

Examples 1–5

Thermoplastic compositions were prepared using varying amounts of a poly(lactic acid) polymer, a polybutylene succinate, and a wetting agent. To prepare a specific thermoplastic composition, the various components were first dry mixed and then melt blended in a counter-rotating twin screw to provide vigorous mixing of the components. The melt mixing involves partial or complete melting of the components combined with the shearing effect of rotating mixing screws. Such conditions are conducive to optimal blending and even dispersion of the components of the thermoplastic composition. Twin screw extruders such as a Haake Rheocord 90, available from Haake GmbH of Karlsautte, Germany, or a Brabender twin screw mixer (cat no 05–96–000) available from Brabender Instruments of South Hackensack, N.J., or other comparable twin screw extruders, are well suited to this task. The melted composition is cooled following extrusion from the melt mixer by forced air passed over the extrudate. The cooled composition is then subsequently pelletized for conversion to fibers.

Converting these resins into fibers was conducted on a in-house 0.75 inch diameter extruder with a 24:1 L:D (length:diameter) ratio screw and three heating zones which feed into a transfer pipe from the extruder to the spin pack, which constitutes the 4th heating zone and contains a 0.62 inch diameter Koch® SMX type static mixer unit, available from Koch Engineering Company Inc. of New York, N.Y., and then into the spinning head (5th heating zone) and through a spin plate which is simply a plate with numerous small holes through which the molten polymer will be extruded through. The spin plate used herein had 15 to 30 holes, where each hole has a 20 mil diameter. The fibers were air quenched using air at a temperature range of 13° C. to 22° C., and drawn down by a mechanical draw roll and passed on to either a winder unit for collection, or to a fiber drawing unit for spunbond formation and bonding, or through accessory equipment for heat setting or other treatment before collection.

The polymers were converted to a spunbond nonwoven material and were performed using 14" and 20" fiber spinning lines. A monocomponent fiber was produced from a single extruder and the fibers were drawn and laid through a fiber draw unit (FDU). The webs were then thermally bonded inline with a wire-weave bond pattern.

The wettability of the nonwoven material Examples was quantified through the use of contact angle measurement, wherein a lower contact angle is indicative of a more wettable material, Contact angle measurements were performed on the Cahn DCA-322 Dynamic Contact Angle Analyzer using the WinDCA version 1.02 analysis software. Resins were spun into freefall fibers to be used in this measurement. Extensive care was taken that the samples were not handled extensively to help prevent contamination. A single fiber approximately 3 cm long was attached to a thin wire hanger with tape such that 1.5 cm of the fiber extended beyond the end of the hanger. The fiber diameter was measured with the use of an optical microscope and entered into the computer. Other parameters such as fiber shape and surface tension of the liquid to be used were also entered into the software. For these Examples, distilled water was used as the liquid.

The fiber was hung from the "A" loop balance and a small beaker of water was placed beneath it so that the end of the fiber was almost touching the surface of the liquid. The stage holding the fiber advanced at 151.75 microns/second until it detected the Zero Depth of Immersion (ZDOI) when the fiber contacted the surface of the distilled water. From the ZDOI, it advanced 1 cm, dwelled for 0 seconds, then immediately receded 1 cm. The data analysis was performed automatically by the analysis software. Each sample was tested five times and the average values were calculated for both advancing and receding contact angles.

The results for advancing and receding contact angles are given in Table 2. The advancing contact angle is a measure of how a material will interact with fluid during its first contact with liquid. The receding contact angle is an indication of how the material will behave during multiple insults with liquid or in a damp, high humidity environment. The blends included in this invention produced highly wettable fibers.

TABLE 2

Contact Angle Data

| Material | Advancing Contact Angle | Receding Contact Angle |
| --- | --- | --- |
| PLA:PBS:Unithox ® (78:9:13) | 71 | 44 |
| PLA:PBS:Unithox ® (86:9:5) | 73 | 44 |
| PLA:PBS:Unithox ® (87:10:3) | 77 | 49 |
| PLA:PBS:Unithox ® (89:10:1) | 79 | 55 |
| Polypropylene | 128 | 94 |

Table 3 gives the results for the fluid management properties of the nonwoven materials of the present invention. As the table demonstrates, the nonwoven materials of the present invention have a much faster intake time than the control surfactant-treated polypropylene spunbond liner. With subsequent insults, the surfactant begins to wash off the treated diaper liner and the intake times rise significantly. The permanently hydrophilic surface of the nonwoven material of the present invention remains permanently wettable, so that while intake times increase, they remain much lower than those for the polypropylene liner. In addition, the liner made using the nonwoven material of the present invention also demonstrates a lower Flowback than the control liner. This low flowback is significant because it indicates that under pressure, very little fluid will flow back to the user side of the liner, keeping skin drier.

One of the most significant tests for skin dryness is how the material behaves in a TEWL test, which measures skin dryness when covered with a diaper insulted with saline. The lower TEWL value demonstrated by the nonwoven material of the present invention indicates an improvement in skin dryness.

TABLE 3

Fluid Management Properties

| | Control-0.5 osy polypropylene spunbond | 0.8 osy PLA:PBU:Unithox ® blend |
| --- | --- | --- |
| FIFE - 1$^{st}$ Insult Time (sec) | 28.03 | 22.68 |
| FIFE - 2$^{nd}$ Insult Time (sec) | 83.03 | 54.08 |
| FIFE - 3$^{rd}$ Insult Time (sec) | 94.98 | 55.95 |
| Flowback (grams) | 3.40 | 1.99 |
| TEWL (g/m$^2$) | 22.1 | 19.1 |

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A method of forming a multi-component fiber comprising:

extruding a thermoplastic composition blend; and spinning the extruded thermoplastic composition blend into a continuous multi-component fiber;

wherein the multi-component fiber exhibits an Advancing Contact Angle value that is less than about 80 degrees and a Receding Contact Angle value that is less than about 60 degrees.

2. The method of claim 1, wherein the thermoplastic composition blend comprises:

a. a poly(lactic acid) polymer in a weight amount that is greater than 0 but less than 100 weight percent;

b. a polymer selected from the group consisting of a polybutylene succinate polymer, a polybutylene succinate adipate polymer, and a mixture of such polymers, in a weight amount that is greater than 0 but less than 100 weight percent; and c. a wetting agent, which exhibits a hydrophilic-lipophilic balance ratio that is between about 10 to about 40, in a weight amount that is greater than 0 to about 15 weight percent, wherein all weight percents are based on the total weight amount of the poly(lactic acid) polymer; the polymer selected from the group consisting of a polybutylene succinate polymer, a polybutylene succinate adipate polymer, and a mixture of such polymers; and the wetting agent present in the thermoplastic composition.

3. The method of claim 2, wherein the poly(lactic acid) polymer is present in a weight amount that is between about 5 weight percent to about 95 weight percent, the polymer selected from the group consisting of a polybutylene succinate polymer, a polybutylene succinate adipate polymer, and a mixture of such polymers, is present in a weight amount that is between about 5 weight percent to about 95 weight percent, and the wetting agent is present in a weight amount that is between about 0.5 weight percent to about 15 weight percent.

4. The method of claim 2, wherein the wetting agent exhibits a hydrophilic-lipophilic balance ratio that is between about 10 to about 20.

5. The method of claim 2, wherein the wetting agent is an ethoxylated alcohol.

6. The method of claim 1, wherein the multicomponent fiber exhibits an Advancing Contact Angle value that is less than about 75 degrees and a Receding Contact Angle value that is less than about 55 degrees.

7. The method of claim 6, wherein the difference between the Advancing Contact Angle value the Receding Contact Angle value is less than about 30 degrees.

8. The method of claim 1, wherein the multicomponent fiber exhibits a Heat Shrinkage value that is less than about 15 percent.

9. A method of forming a multi-component fiber comprising:

extruding a thermoplastic composition blend;

spinning the extruded thermoplastic composition blend into a continuous multi-component fiber;

cooling, solidifying and drawing the continuous multi-component fiber to an intermediate filament diameter;

drawing the intermediate multi-component fiber at a temperature below its softening point to a desired finished fiber diameter; and cutting the finished multi-component fiber into desirable lengths to form short-cut or staple multi-component fibers;

wherein the multi-component fiber exhibits an Advancing Contact Angle value that is less than about 80 degrees and a Receding Contact Angle value that is less than about 60 degrees.

10. The method of claim 9, wherein the thermoplastic composition blend comprises:

a. a poly(lactic acid) polymer in a weight amount that is greater than 0 but less than 100 weight percent;

b. a polymer selected from the group consisting of a polybutylene succinate polymer, a polybutylene succinate adipate polymer, and a mixture of such polymers, in a weight amount that is greater than 0 but less than 100 weight percent; and c. a wetting agent, which exhibits a hydrophilic-lipophilic balance ratio that is between about 10 to about 40, in a weight amount that is greater than 0 to about 15 weight percent, wherein all weight percents are based on the total weight amount of the poly(lactic acid) polymer; the polymer selected from the group consisting of a polybutylene succinate polymer, a polybutylene succinate adipate polymer, and a mixture of such polymers; and the wetting agent present in the thermoplastic composition.

11. The method of claim 10, wherein the poly(lactic acid) polymer is present in a weight amount that is between about 5 weight percent to about 95 weight percent, the polymer selected from the group consisting of a polybutylene succinate polymer, a polybutylene succinate adipate polymer, and a mixture of such polymers, is present in a weight amount that is between about 5 weight percent to about 95 weight percent, and the wetting agent is present in a weight amount that is between about 0.5 weight percent to about 15 weight percent.

12. The method of claim 10, wherein the wetting agent exhibits a hydrophilic-lipophilic balance ratio that is between about 10 to about 20.

13. The method of claim 10, wherein the wetting agent is an ethoxylated alcohol.

14. The method of claim 9, wherein the multicomponent fiber exhibits an Advancing Contact Angle value that is less than about 75 degrees and a Receding Contact Angle value that is less than about 55 degrees.

15. The method of claim 14, wherein the difference between the Advancing Contact Angle value the Receding Contact Angle value is less than about 30 degrees.

16. The method of claim 9, wherein the multicomponent fiber exhibits a Heat Shrinkage value that is less than about 15 percent.

* * * * *